United States Patent [19]

Manske

[11] 4,098,120
[45] Jul. 4, 1978

[54] HUMIDITY INDICATING METHOD AND DEVICE

[75] Inventor: Wendell J. Manske, Birchwood Village, Minn.

[73] Assignee: Minnesota Mining and Manufacturing Company, Saint Paul, Minn.

[21] Appl. No.: 584,472

[22] Filed: Jun. 6, 1975

[51] Int. Cl.² .............................................. G01W 1/00
[52] U.S. Cl. .................................................... 73/335
[58] Field of Search ...................... 73/29, 61.1 R, 335; 116/114 AM; 23/253 TP

[56] References Cited

U.S. PATENT DOCUMENTS

| | | | |
|---|---|---|---|
| 1,625,420 | 4/1927 | Patterson | 73/335 |
| 2,249,867 | 7/1941 | Snelling | 73/335 |
| 3,006,313 | 10/1961 | Huyck et al. | 116/114 V |
| 3,198,163 | 8/1965 | Williams | 116/114 AM |
| 3,243,303 | 3/1966 | Johnson | 99/192 |
| 3,420,205 | 1/1969 | Morison | 116/114 AM |
| 3,479,877 | 11/1969 | Allen et al. | 73/358 |
| 3,620,677 | 11/1971 | Morison | 23/253 TP |
| 3,677,088 | 7/1972 | Lang | 73/356 |

OTHER PUBLICATIONS

Maximum Humidity Indicator, Bendix Corporation Report BDX-613-1150 for U.S. AEC. available from National Technical Information Service.
Deliquescent-Chemical Maximum Humidity Indicator, Bendix Corp. Report BDX-613-921 for U.S. AEC., available from National Technical Information Service.

*Primary Examiner*—Donald O. Woodiel
*Attorney, Agent, or Firm*—Cruzan Alexander; Donald M. Sell; Warren R. Bovee

[57] ABSTRACT

Humidity indicating method and device suitable for visibly indicating exposure to a selected humidity level or for indicating a humidity-time history. The device comprises in combination a deliquescent compound, a liquid absorbent wick, and an indicating means. The change in properties of deliquescent compounds are employed to indicate a particular humidity level or a humidity-time history. Preferred methods of making humidity indicating devices are described.

12 Claims, 10 Drawing Figures

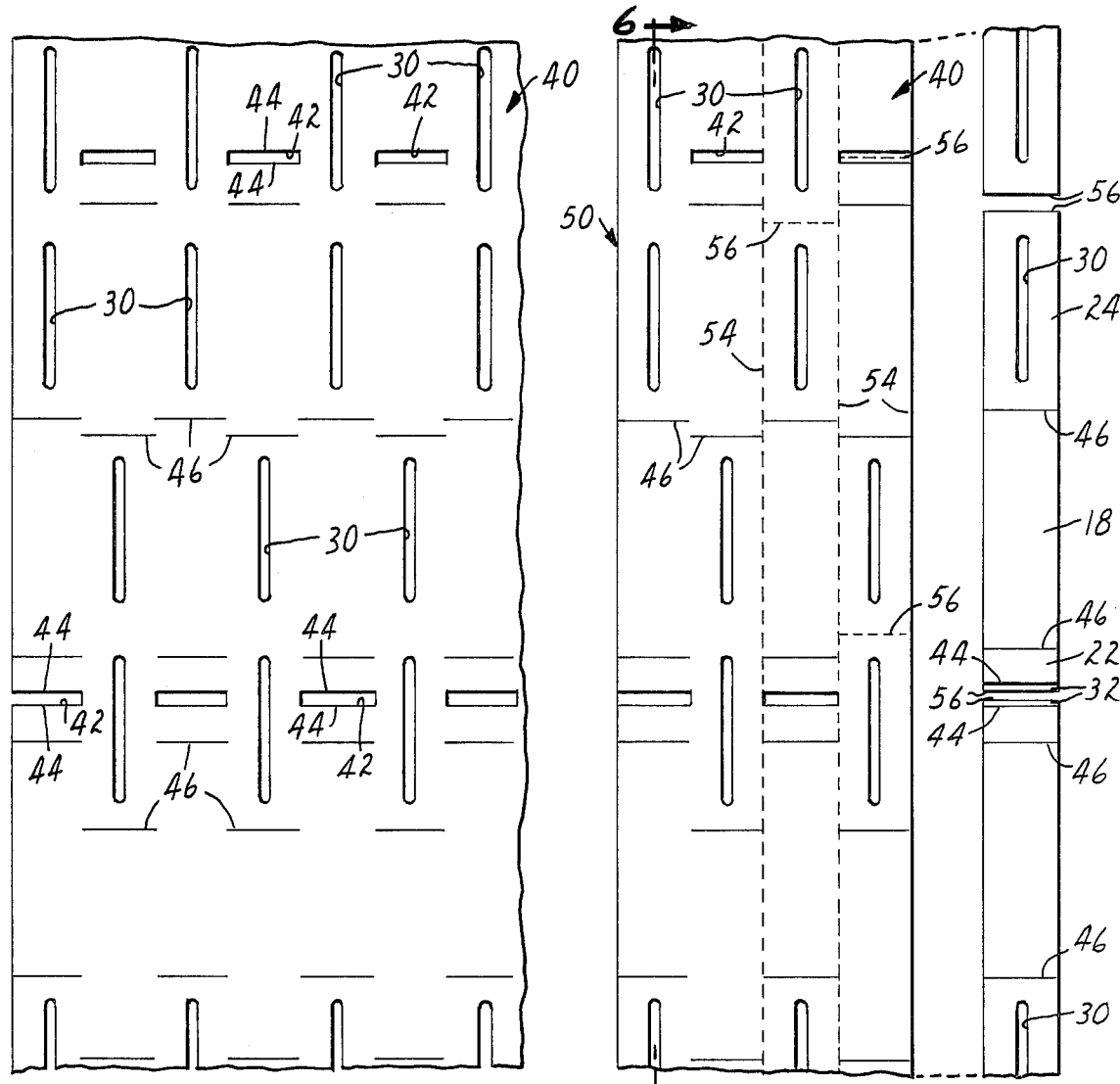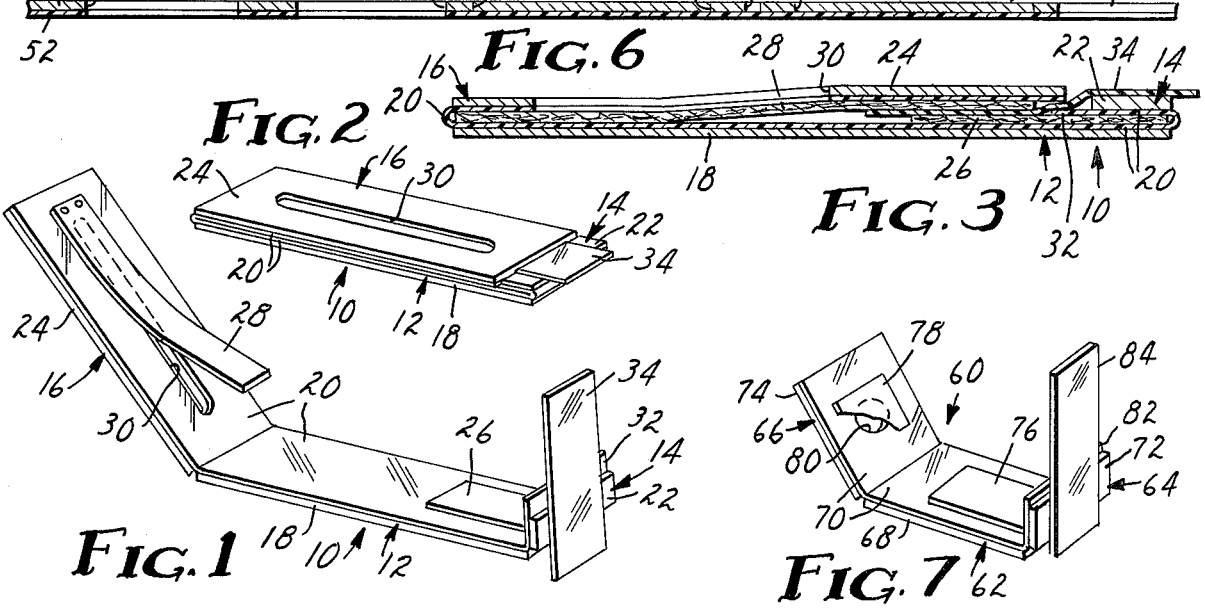

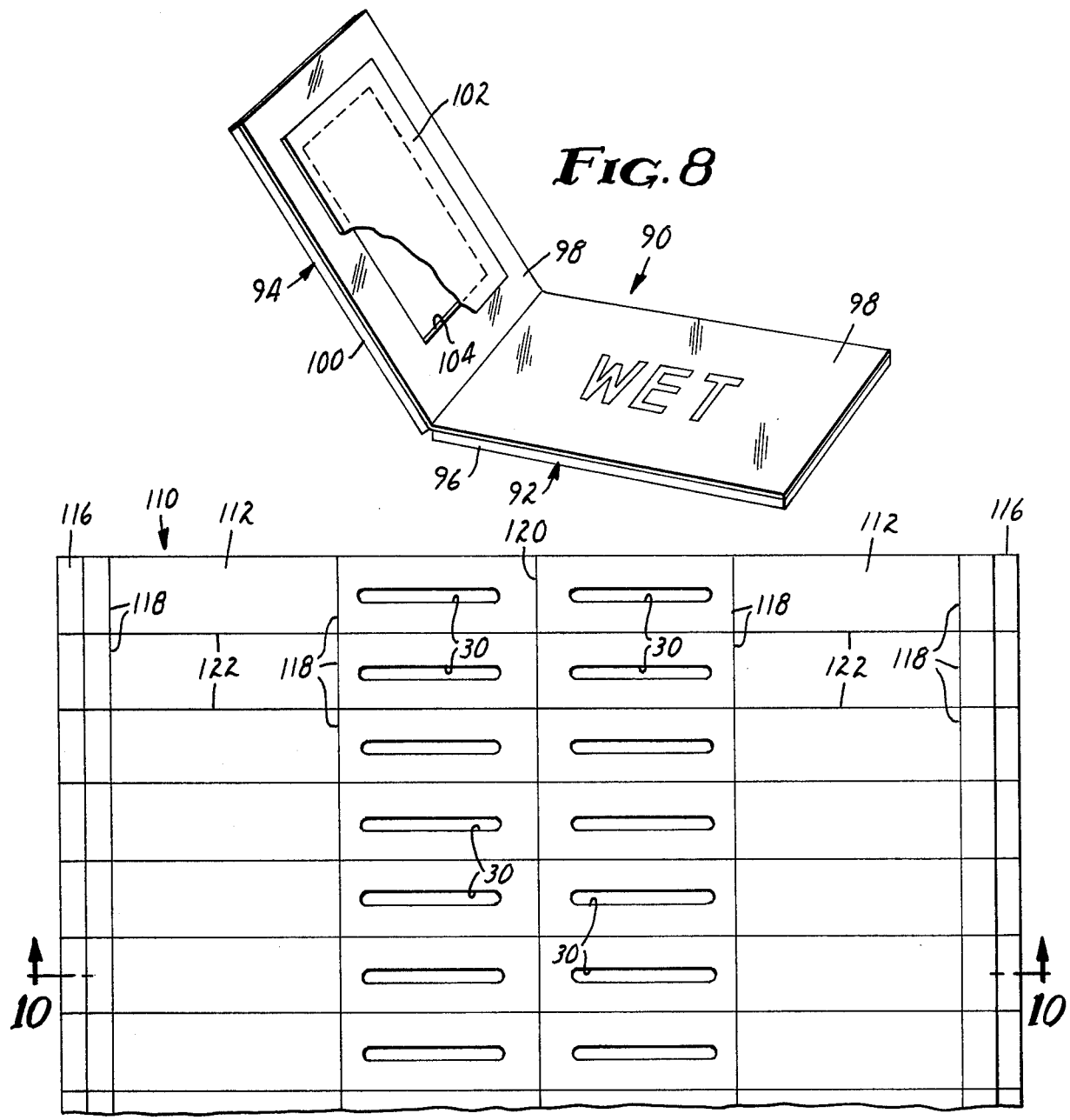
FIG. 8
FIG. 9
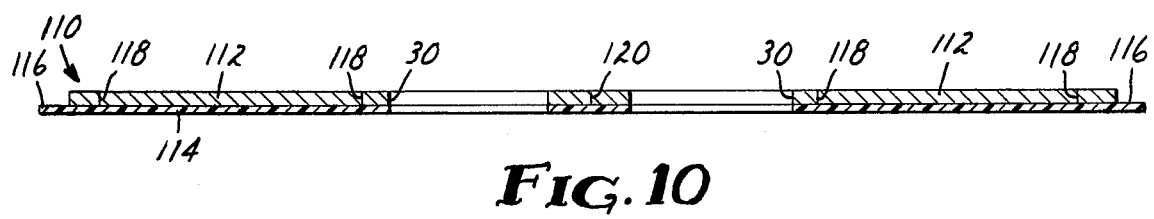
FIG. 10

HUMIDITY INDICATING METHOD AND DEVICE

The present invention relates to a method and means for indicating exposure to or the presence of a selected level of humidity and means for indicating a humidity-time function. The devices described herein are simple, reliable and compact and can be economically mass produced. The devices of the present invention employ humidity responsive indicating materials which deliquesce and effloresce in response to selected levels of relative humidity and operate to visibly indicate the humidity level to which the device is exposed or the humidity history which the device has experienced. Means for controlling the humidity level to which the device will respond and means for correlating the visible indication to the humidity and/or humidity history are described.

A method of making an extremely compact, simple, and reliable humidity indicating device is also described as a part of this invention.

Many articles of commerce such as food, pharmaceuticals, electronic equipment, etc. are sensitive to given levels of humidity. For example, pharmaceuticals may lose their potency and metallic apparatus or electrical equipment may corrode or otherwise be degraded by excessive moisture. Accordingly, there is a need for a simple, economical, and reliable means for determining the humidity levels to which articles of commerce are or have been exposed and in some cases for monitoring and indicating the humidity history, e.g., humidity-time function, to which the article of commerce has been exposed.

A variety of devices have been used to indicate exposure of an article of commerce to a selected level of humidity. Generally, these devices employ cobalt salts which change color on exposure to a selected level of relative humidity. See, for example, U.S. Pat. Nos. 2,526,938, 2,627,505, 3,084,658 and the patents and literature references cited in the prior art discussion in U.S. Pat. Nos. 3,680,364 and 3,788,128. This type of prior art humidity indicator is not satisfactory in that the color change is not always easily recognized, and, because the color change is reversible, the device does not permanently record the exposure to the selected humidity level.

Humidity indicators employing deliquescent salts which change optical properties on changing from the deliquescent to the efflorescent state are disclosed in the aforementioned U.S. Pat. Nos. 3,776,038 and 3,863,502. Polarization techniques are used to provide an indicator capable of providing a visible change in response to changes in relative humidity.

Chemical humidity indicators employing deliquescent salts in combination with water soluble dyes have also been developed. These indicators employ a water soluble dye admixed with a dry deliquescent salt to form a stable system. When the indicator is exposed to a humidity level above the salts' deliquescent point the dye is solubilized and produces a dramatic color change. The change is total and irreversible, and accordingly this type of indicator is used to indicate a single past exposure to a given level of relative humidity. Indicators of this type are described in a report entitled "Maximum Humidity Indicator" prepared by the Bendix Corporation, Kansas City, Mo., Report No. BDX-613-1150(Rev.), October 1974.

The present invention has overcome the disadvantages of the prior art by providing a method of indicating a humidity history comprising exposing a deliquescent compound to humidity and providing means to indicate, and in some cases record, the change in state of the compound in response to changes in relative humidity. For example, the change in optical properties may be observed or the degree of migration, if any, of the deliquescent compound through a liquid-absorbent medium in contact with the compound can be observed.

Humidity indicators comprise deliquescent compounds such as inorganic salts or organic compounds which are uniquely combined with means to monitor, and in some cases permanently record, exposure of the deliquescent compounds to selected levels of relative humidity or record a humidity-time history.

The ability of deliquescent salts to absorb moisture and form aqueous solutions under certain relative humidity conditions is well known. The present invention utilizes the capability of certain inorganic salts and organic compounds to deliquesce and effloresce when utilized in unique combinations wherein the deliquescent compounds absorb moisture to form aqueous solutions which migrate to and throughout a wick, or which exhibit altered optical properties, to provide a visible indication, and in some cases a permanent record, of exposure to a given relative humidity or a humidity-time history.

One embodiment of a humidity indicator according to the present invention comprises, in combination, a porous matrix carrying a deliquescent compound such as an inorganic salt or organic compound which is capable of absorbing moisture to form an aqueous solution and a wick capable of wicking aqueous liquid from the matrix. In addition, means for regulating migration of the aqueous solution from the matrix to the wick may be included. The regulating means can be a barrier layer removably interposed between the matrix and the wick or other means for temporarily separating the matrix and the wick. The combination includes means for indicating the presence of the aqueous liquid in the wick.

The indicating means can be a naturally colored solution of the deliquescent compound, a readily-visible, water-soluble dye admixed with the deliquescent compound, or an indicating component admixed with the deliquescent compound which will respond to a second component in the wick to form a visibly colored material, such as a pH sensitive dye, a colorforming chemical complexing agent or the like. Alternatively, the indicating means can be means for measuring electrical resistance in the wick.

Exposure of the device to a relative humidity above the deliquescent point of the deliquescent compound causes the compound to form an aqueous solution and migrate along or through a wick to provide an observable change in the wick, such as a visible color change throughout all or a part of the wick.

Humidity indicating devices wherein a lengthened wick is employed to provide an extended migration path for the aqueous solution formed in the porous matrix are uniquely suited for recording humidity-time histories. Thus, exposure of the device to a selected level of relative humidity will cause the aqueous solution to form and migrate along the wick. The rate of migration can be empirically correlated to the humidity level and the elapsed time at the particular humidity level. Thus, the device of the present invention, when attached to an article of commerce, can provide a visible indication which can be correlated to a known humidity history for the article to which it is attached.

Another embodiment of the humidity indicating device of the present invention comprises, in combination, a coherent, continuous layer of deliquescent compound which is opaque at humidity levels below the point at which the compound deliquesces and which becomes optically transparent on deliquescing, together with a layer underlying the deliquescent compound which is at least partially colored in contrast to the opaque compound so as to be observable, and preferably conspicuous, when the compound deliquesces and become transparent.

When the humidity is below a given level, the deliquescent compound remains opaque and the underlying layer is not visible. When the humidity rises above the point at which the compound deliquesces, the compound becomes transparent and the underlayer is visible, preferably conspicuous, to the observer indicating exposure to a selected level of relative humidity. When the humidity level is again lowered below the deliquescent point of the compound, the compound effloresces and again becomes opaque and the underlayer is no longer visible to the observer. In one embodiment of the invention the underlayer can be a contrasting color or can have intelligence printed on the surface thereof so that when the deliquescent compound becomes transparent a conspicuous color or a message, such as "wet" or "90% R.H." or other appropriate message will be conveyed to the observer.

The present invention can be more clearly understood by reference to the following illustrations wherein FIG. 1 is a perspective view of the elements of a humidity indicating device prior to final assembly;

FIG. 2 is a perspective view of an assembled humidity indicating device;

FIG. 3 is a cross section of the assembled device shown in FIG. 2;

FIG. 4 is a top view of a sheet component useful in the manufacture of the device shown in FIGS. 1, 2 and 3;

FIG. 5 is a top view of a plastic surfaced sheet containing pre-cut components useful in making the humidity indicators of the present invention;

FIG. 6 is a cross section along line 6—6 of the sheet of FIG. 5;

FIG. 7 is a perspective view showing an alternate embodiment of a humidity indicating device prior to final assembly;

FIG. 8 is a perspective view showing an embodiment of a reversible humidity indicating device according to the present invention;

FIG. 9 shows a sheet having a plastic film adhered thereto useful in making components for a humidity indicating device; and FIG. 10 is a cross section along line 10—10 of the sheet of FIG. 9.

Referring particularly to FIGS. 1 through 3, a humidity indicating device 10 is shown comprising base 12, and cover means comprising first cover 14 and second cover 16. Base 12 comprises an elongated sheet 18 having adhered to and covering the surface a transparent impervious film 20 such as a polyethylene film or other plastic film. Similarly, covers 14 and 16 comprise sheets 22 and 24 having an adhered covering of transparent impervious film 20 covering all of the surface except for the viewing and sensing opening 30 in sheet 24. In this area, film 20 is perforated or cut out to form an opening in cover 16. If film 20 is cut in the outline of opening 30, the opening in film 20 should be slightly smaller than opening 30 to protect the edges of opening 30 from the liquid in wick 28. These openings allow pad 26 and wick 28 to be exposed to the humidity in the environment. Sheets 18, 22 and 24 can be any semi-rigid material which can be cut, folded and flexed to provide the device described herein. Paperboard is generally preferred for reasons of economy. The plastic film 20 can be adhered to the sheets 18, 22 and 24 by any suitable means, such as by adhesive bonding, heat sealing, spot welding, or the like.

A porous reservoir pad 26 is located on base 12, preferably proximate cover 14 as shown in FIGS. 1 and 3. The reservoir pad 26 may be paper or other porous absorbent material. Preferably the reservoir pad 26 is a piece of blotting paper. The reservoir pad 26 may be adhered to base 12 if desired, although in the embodiment shown in FIGS. 1 through 3 this is not necessary since pad 26 is securely held in the assembled indicator by its relation to cover 14. Reservoir pad 26 contains a humidity indicating material comprising a deliquescent salt and, optionally, a water soluble dye if needed to provide color. The various deliquescent salts useful in the humidity indicating devices of this invention will be described in greater detail hereinafter.

Wick 28 is shown adhered to second cover 16 and is positioned overlying viewing and sensing window 30 in cover 16. The wick shown in FIGS. 1 through 3 is an elongated piece of absorbent material such as blotter paper, filter paper or the like which will absorb aqueous liquids and allow migration of the liquids throughout the wick. Other wick materials can be used with advantage such as films deposited from starch slurries and silica sols, compacted powder such as diatomaceous earth and talc, and other materials having a sufficiently fine porosity to form capillaries through which the aqueous salt solutions which are formed in the reservoir pad 26 will flow when wick 28 and pad 26 are in intimate contact.

Protective tab 32 is shown extending from cover 14. Tab 32 is a impervious material which, in assembled humidity indicator 10, overlies a portion of pad 26 to protect the abutting edges of covers 14 and 16 from the liquid material which may be formed in pad 26. Alternatively, tab 32 could be a separate barrier strip overlying a portion of pad 26 and underlying the abutting edge portions of covers 14 and 16. Yet another alternative is to seal the portion of pad 26 underlying the abutting edges of covers 14 and 16 so that the material in pad 26 will not be available in the sealed area of the pad.

Activator strip 34 is an optional feature of this embodiment and is an impervious film such as a plastic strip which, when in place, prevents contact between pad 26 and wick 28. Activator strip 34 may be removably adhered to cover 14 to prevent accidental removal of strip 34. When in place, the strip 34 prevents migration of liquid between pad 26 and wick 28 when exposed to high humidity during storage. If care is taken to prevent the indicator 10 from being exposed to high humidity during storage, such as by packing in a sealed container, activator strip 34 may be eliminated so that the indicator will be in a permanently activated state.

To seal device 10 and to bias wick 28 toward pad 26, the open sides of the indicator 10 between base 12 and covers 14 and 16 are brought into contact and sealed or bonded along the edges such as by heat sealing, by using an adhesive, or by the use of mechanical fasteners such as staples or the like. Thus, when the edges of the covers are sealed, the only openings in indicator 10 are the slot between abutting covers 14 and 16 through which activator strip 34 extends and viewing and sensing window 30.

In use, reservoir pad 26 has absorbed therein a desired concentration of deliquescent salt and optionally a visible dye which is in the dry state. When the humidity indicating device is exposed to a humidity level above the deliquescent point of the salt in reservoir pad 26, the salt deliquesces, that is the salt absorbs water vapor from the surrounding environment forming a saturated solution, and migrates from reservoir pad 26 along and through wick 28. The distance which the indicating material migrates along wick 28 can be visibly measured due to the color of the salt solution or the presence of the visible dye and can be correlated with a known humidity-time history. If the humidity falls below the deliquescent point of the salt, the salt in the reservoir pad 26 and wick 28 gives up water and effloresces, and no further migration occurs until the humidity again exceeds the deliquescent point of the salt. Thus, the device records the cumulative time during which the device has been exposed to a relative humidity above the deliquescent point of the particular salt employed.

The rate of migration varies somewhat at different humidity levels above the deliquescent point of the particular salt used in the indicator. In practice, duplicate indicators may be exposed to various constant humidity levels and the rate of migration plotted against time. The curves generated can then be used to determine the humidity-time history of an indicator which has been exposed to an unknown humidity environment.

When assembled, the device can be stored for long periods of time prior to use. Accidental exposure to humidities above the deliquescent point of the salt do not harm the device when activator strip 34 is present. The strip prevents migration of liquid from reservoir pad 26 to wick 28, and accordingly, the device is not "activated" until the strip 34 is removed.

The physical dimensions of wick 28 can be varied to provide a device capable of recording relatively long humidity histories. In addition, the concentration of deliquescent salt initially provided in reservoir pad 26 can be used to regulate the driving force for migration along wick 28. If the initial concentration is low, the migration rate along wick 28 will be rather slow and the device can be used to record extremely long humidity histories. If the initial concentration of salt in reservoir pad 26 is very high, pad 26 will absorb relatively large quantities of water, the driving force for migration along wick 28 will be high and the rate of travel along wick 28 relatively fast. A device having a rapid migration rate might be useful where sensitivity to relatively short exposure to given levels of humidity is required.

FIGS. 4, 5 and 6 show sheets used in one method of manufacture of humidity indicators of the type shown in FIGS. 1 through 3.

In FIG. 4 a portion of a paperboard sheet 40 is shown containing a patterned plurality of rectangular openings 42 having long edges 44. The long edges 44 of rectangular openings 42 are located to form the ends of a pair of opposed cover sheets 22 of indicator 10 shown in FIGS. 1 through 3. Said horizontal lines 46 represent cut lines through sheet 40 and are located to define the abutting ends of cover sheets 18, 22 and 24 of the indicator 10 shown in FIGS. 1-3.

FIGS. 5 and 6 show the sheet 40 of FIG. 4 after being further processed. Sheet 50 of FIG. 5 comprises paperboard sheet 40 having an impervious plastic film 52 laminated to the underside thereof. Viewing and sensing openings 30 are cut through sheet 40 and film 52. Sheet 50 is cut into rectangular pieces by cutting along vertical lines 54 and horizontal lines 56. The resulting elongated rectangular pieces are divided into portions corresponding to base 12, and cover portions 14 and 16 of FIGS. 1 through 3 by lines 46 which were cut through sheet 40, but not film 52. Alternatively lines 46 could be score lines which are perforations or bar score lines made by compressing sheet 50 along lines 46 without cutting either paperboard sheet 40 or the plastic film 52. The score lines 46 allow the rectangular pieces to be readily folded to form the indicator shown in FIGS. 1 through 3.

FIG. 7 shows another embodiment of the present invention which is particularly useful as a telltale monitoring device for irreversibly indicating a one time exposure to a given humidity level. In this embodiment, indicator 60 comprises a base 62 and cover means comprising a first cover 64 and a second cover 66. Base 62 comprises a sheet 68 having adhered to the surface an impervious film 70. Similarly, covers 64 and 66 comprise sheets 72 and 74 having an adhered covering of an impervious film 70. Film 80 is cut out or perforated in the area of opening 80 as discussed with regard to the embodiments shown in FIGS. 1-3.

A porous reservoir pad 76 is located on base 62 proximate first cover 64. Pad 76 contains a dry composition comprising a deliquescent salt, and, if desired, a water soluble dye if the deliquescent salt is colorless.

Wick 78 is shown as a small pad located on, and adhered to, second cover 66 so that a portion of wick 78 is visible through viewing and sensing opening 80. Protective tab 82 is shown extending from cover 64. When covers 64 and 66 are consecutively folded over base 62, tab 82 overlies a portion of reservoir pad 76 and protects the abutting edges of covers 64 and 66 from the liquid which forms in reservoir pad 76 during use. Alternatively, tab 82 can be replaced by a separate strip of impervious material partially covering pad 76 and protecting the abutting edges of covers 64 and 66 from the liquid which forms in pad 76. Yet another means of protecting abutting edges of covers 64 and 66 is by the application of an impervious film-forming liquid to a portion of pad 76 underlying the abutting edges of covers 64 and 66.

Activating strip 84 is, as with the embodiments discussed previously, optional, and is an impervious strip, such as a plastic strip, which, when in place in the assembled indicator, prevents contact between pad 76 and wick 78. Activator strip 84 may be removably adhered to cover 64 to prevent accidental removal of the activator strip.

Cover 64 is folded over base 62 and the activator strip 84 set in place overlying pad 76 and extending over cover 64. Cover 66 is subsequently folded over base 62 abutting cover 64. The sides of the cover 64 and 66 and base 62 are then bonded together to seal the indicator 60 and bias wick 78 toward reservoir pad 76.

When activator strip 84 is removed from indicator 60 no migration takes place between pad 76 and wick 78 while the device is exposed to humidities below the deliquescent point of the salt in pad 76 since there is no liquid in pad 76. However, when the device is exposed to humidities above the deliquescent point of the salt in reservoir pad 76, the salt absorbs water vapor and forms a colored, aqueous solution. The aqueous solution then migrates into wick 78, coloring the wick. The color change in the wick is quickly observed through viewing window 80. Thus, the device quickly indicates exposure to a minimum level of humidity. The device is irreversible in that the color remains in wick 78 even though the humidity level again drops below the deliquescent point of the salt in pad 76.

FIG. 8 shows a reversible humidity indicating device 90 according to the present invention. In this embodiment, indicator 90 comprises a base 92 and cover means 94. Base 92 comprises a sheet 96 having adhered to the surface an impervious film 98. Similarly, cover 94 comprises sheet 100 having an adhered covering of impervious film 98. Viewing and sensing opening 104 is shown as an opening in cover 94. Preferably, film 98 is perforated in the area of opening 104, or an opening in the film is cut out inside opening 104 so the edges of opening 104 is protected by film 98 from liquid which may be present in reservoir 102. Reservoir 102 is shown overlying viewing and sensing window 104 and adhered to cover 94. As shown in FIG. 8 reservoir 102 is a thin sheet of tissue paper or other light transmitting absorbent material saturated with a dried deliquescent salt which is opaque below the deliquescent point and which becomes transparent when it deliquesces.

The surface of base 92 visible through viewing window 104 is colored so as to contrast strongly with the opaque color of reservoir 102. In addition to, or in lieu of, the contrasting color, base 92 can have a legend printed on the surface in register with viewing window 104, such as the word "wet" as shown in FIG. 8 or other appropriate legend such as "80% R.H." or the like so that when reservoir 102 becomes transparent a message will be conveyed to the observer.

Cover 94 is folded over base 92 and the sides of the cover 94 and base 92 are then bonded together to seal the indicator.

In operation, observation of viewing window 104 reveals an opaque color characteristic of the deliquescent salt absorbed in reservoir 102. Generally the useful salts are white in the dry state. When the humidity level to which device 90 is exposed reaches a level above the deliquescent point of the salt in reservoir 102, the salt forms a saturated solution and becomes transparent, revealing to the observer the contrasting color of base 92 or the legend printed thereon. When the humidity level again drops below the deliquescent point of the salt in reservoir 102, the salt effloresces, the reservoir becomes opaque and the contrasting color or legend on base 92 is no longer visible to the observer. Device 90 will continue to repeat the visible changes in response to changes in humidity.

Where the device shown in FIG. 8 will be exposed for long periods to a humidity much higher than the minimum humidity at which the salt in reservoir 102 will deliquesce, the salt can take on too much liquid for the reservoir 102 to hold if it is made of a thin tissue material. Therefore, if exposure to humidities considerably higher than the deliquescent point humidity is expected, a reservoir 102 comprising the deliquescent chemical contained in a cavity which has good moisture vapor transmission, but which will not transmit liquid water, such as for example a cellulose acetate envelope, should be used. Generally this will increase the response time of the indicator, but will prevent harmful effects from the excess liquid absorbed by the deliquescent salt in the reservoir.

FIGS. 9 and 10 show an alternate embodiment of a sheet from which components for making a humidity indicator 10, as shown in FIGS. 1 through 3, can be obtained. Sheet 110 comprises paperboard sheet 112 and an impervious film 114 overlying and adhering to sheet 112 and extending beyond the edges of sheet 112 to form flap 116 along each edge of sheet 110. Openings 30 are cut in sheet 110 (through paperboard sheet 112 and impervious film 114). Preferably the opening in film 114 is slightly smaller than the opening in paperboard sheet 112, or the film is perforated. Sheet 110 is scored along lines 118 such as by cutting through paper sheet 112 or bar scoring sheet 110 along lines 118. Sheet 110 is then cut through along vertical line 120 and horizontal lines 122. This provides rectangular pieces having a viewing and sensing opening 30 therein and a tab 116 on one end, which pieces are suitable for use as base 12 and covers 14 and 16 of the humidity indicator 10 shown in FIGS. 1 through 3. An alternative to cutting the sheet 110 completely through at lines 120 and 122 is to discontinuously cut or perforate the sheet so that the pieces do not separate, but are held together by "hang tabs" until the pieces are finally torn from the sheet by hand.

As noted previously, the indicating devices of the present invention employ the properties of materials which deliquesce at specific relative humidities. Deliquescence refers to the absorption of atmospheric water vapor by a crystalline solid until the crystal eventually dissolves into a saturated solution. This behavior is well known for certain salts such as hydrated calcium chloride, and zinc chloride, but is a property of all soluble salts and other organic compounds in air of sufficiently high humidity. The condition for deliquescence is that the partial pressure of water vapor in air exceed the vapor pressure of the water in the saturated solution of the deliquescent material. Thus, the value of these materials as humidity indicators arises because the absorption of water by the deliquescent materials is dependent on the relative humidity to which the deliquescent material is exposed.

The deliquescent materials useful in the present invention can be any of the inorganic salts or organic compounds which deliquesce at useful humidity levels. Representative materials which have been found useful in the humidity indicators disclosed herein are magnesium nitrate, sugar, cuprous chloride, sodium bromide, nickel nitrate, ferric nitrate, cobalt bromide, ammonium nitrate, sodium dichromate, ferrous chloride, ammonium dichromate, nickel chloride, strontium chloride, and cuprous nitrate. Other deliquescent salts are listed in a report available from the National Technical Information service entitled "Deliquescent-Chemical Maximum Humidity Indicator" prepared by the Bendix Corporation, Kansas City, Missouri, for the Atomic Energy Commission under Contract Number AT(29-1)-613, May 1973.

It may be desirable to use various water soluble dyes with certain of the salts which do not have a visible color of their own. Thus, Neptune Blue BRA dye, rhodamine B dye, and Alphazurine 2 G Blue dye (National Aniline) have been found useful in the present invention. Other useful dyes are known and representative dyes are disclosed in Table 1 of the aforementioned report "Deliquescent-Chemical Maximum Humidity Indicator." Certain of the salts such as nickel nitrate can be used without dyes since they provide a highly visible color by themselves.

For the reversible indicators, such as those shown in FIG. 8 of the drawings, a salt which becomes transparent above the deliquescent point must be used. Representative salts of this type and their approximate deliquescent points are lithium chloride (11% R.H.), potassium acetate (23% R.H.), magnesium chloride (33% R.H.), potassium carbonate (43% R.H.) sodium bromide (57% R.H.), strontium chloride (72% R.H.), and sodium carbonate (90% R.H.).

EXAMPLE 1

A humidity indicator such as shown in FIGS. 1 through 3 of the drawings was prepared using a reservoir pad of blotting paper ("Bluebird" blotting paper, Sorg Paper Company) about 1.25 cm by 5.7 cm and 0.023 cm thick. An aqueous solution of magnesium nitrate containing 0.5% by weight, based on the weight of magnesium nitrate, of a triphenylmethane dye ("Alpha zurine" 2G blue dye, National Aniline) was prepared. The magnesium nitrate solution was absorbed into the filter paper reservoir pad and dried to provide a pad containing 74% by weight, based on the combined weight of the pad and the magnesium nitrate, of salt in the pad.

The wick was prepared from a piece of Whatman No. 4 filter paper having a cross section about 0.023 cm thick and 0.635 cm wide. The wick was about 7.5 cm in length.

The magnesium nitrate salt deliquesces at a relative humidity of about 52%. The humidity indicator was exposed to a relative humidity of 74% and the rate of migration of the blue salt solution along the wick was observed for a period of about 60 hours. At 24 hours the blue solution had migrated about 3.2 centimeters along the wick. At 48 hours exposure to 74% relative humidity, the blue solution had migrated about 5.3 centimeters along the wick. At 60 hours the blue solution was observed to have migrated about 6.1 centimeters along the wick. This data was plotted and was found to be useful in calibrating duplicate humidity indicators capable of monitoring and recording a humidity history.

EXAMPLE 2

A pair of humidity indicators was prepared as described in Example 1 except that the wicks were made from the same blotting paper as the reservoir pad. A saturated solution of nickel nitrate in water was prepared and absorbed into the reservoir pad of each of the indicators. The first indicator was provided with a reservoir pad containing about 64% by weight nickel nitrate, based on the combined weight of the pad and the dried nickel nitrate. The second indicator was provided with a pad containing about 54% by weight of the nickel nitrate.

The indicators were exposed to a relative humidity of 67%. Since this humidity level was above the deliquescent point of nickel nitrate, the nickel nitrate in each indicator formed an aqueous solution and began to migrate along the wick and impart a green color to the wick. Because the reservoir pads in each indicator contained different amounts of nickel nitrate, the driving force, and hence the migration rates along the wick were different. After 500 hours exposure to 67% relative humidity, the indicator containing the lower concentration of salt in the reservoir pad had migrated about 2 centimeters along the wick. The indicator containing the higher concentration of salt in the reservoir pad had migrated approximately 3.6 centimeters along the wick during the 500 hour exposure. After 1100 hours exposure to the 67% relative humidity environment, the indicator having the lower concentration showed a migration front about 2.5 centimeters along the wick, whereas the indicator having the higher concentration of salt in the reservoir had migrated about 4.3 centimeters along the wick during the same time period.

EXAMPLE 3

A reversible humidity indicator was prepared by bonding a thin sheet of tissue paper to one side of a sheet of clear transparent polyethylene. A number representing a relative humidity was printed on the other side of the polyethylene sheet so as to be visible through the tissue. The tissue was then treated with a saturated aqueous solution of sodium bromide and dried. Upon drying, the tissue became opaque and the number could not be seen through the tissue. When the indicator was placed in an environment having a relative humidity above 57%, the deliquescent point of the sodium bromide salt, the tissue became transparent and the number was visible through the tissue. When the indicator was placed in an environment having a relative humidity below 57%, the salt in the tissue effloresced and became opaque and the number was no longer visible through the tissue.

I claim:

1. A device for indicating a humidity history comprising, in combination, a porous pad containing a deliquescent compound, an elongated wick capable of wicking liquid from said pad, and means for directing migration of available liquid in said pad through said wick to provide a visible, migrating front of liquid in said wick.

2. A device according to claim 1 wherein said pad is capable of containing a selected concentration of deliquescent compound and presenting a controlled amount of liquid to said wick thereby selectively controlling the maximum migration rate of said available liquid through said wick.

3. A device according to claim 2 including moisture barrier means for temporarily preventing migration of said deliquescent compound from said pad to said wick.

4. A device according to claim 3 wherein said moisture barrier means is a moisture impermeable container enclosing said device.

5. A device according to claim 3 wherein said moisture barrier means is a moisture impermeable layer removably interposed between said pad and said wick.

6. A device according to claim 3 wherein said deliquescent compound is an inorganic salt.

7. A device according to claim 3, wherein said matrix and said wick are liquid-absorbent paper.

8. a humidity indicating device comprising, in combination,
a base sheet;
a porous reservoir pad located proximate one end of said base sheet;
a deliquescent indicating compound contained within said pad;
a cover overlying and substantially coextensive with said base sheet, said cover having an opening therein;
a wick contained between said cover sheet portion and said base sheet, at least a portion of said wick being visible through the opening in said cover sheet portion and a portion of said wick lapping at least a portion of said reservoir pad to provide an observable extended migration path for said indicating compound; and means for biasing said wick towards said pad.

9. A humidity indicating device comprising, in combination,
a base sheet having first and second ends;
a porous reservoir pad located proximate said first end of said base sheet;
a deliquescent compound contained within said pad;
a cover overlying and substantially coextensive with said base sheet, said cover comprising first and second abutting cover sheet portions with said first cover sheet portion extending from said first end of said base sheet and having its edge abutting said second cover sheet portion transverse of said reservoir pad, and said second cover sheet portion extending to said second end of said base sheet and having an opening therein;
a protective strip comprising liquid impervious film underlying the abutting edges of said first and second cover sheet portions and interposed between said reservoir pad and the abutting edges on said first and second cover sheet portions to protect the adjacent edges of said first and second cover sheet portions from the liquid which may be absorbed in the reservoir pad;
a wick adhered to said second cover sheet portion and contained between said second cover sheet portion and said base sheet, at least a portion of said wick being visible through the opening in said second cover sheet portion and at least a portion of said wick lapping at least a portion of said reservoir pad;
a means for biasing said wick towards said pad; and
a liquid impervious activating strip having one end portion positioned between and covering the adjacent surface portions of said wick and said reservoir pad, and having its opposite end portion extending between and projecting from the abutted ends of said first and second cover sheet portions to afford manual engagement to pull said activating strip from between said pad and wick to thereby allow intimate contact of said pad and said wick.

10. A reversible humidity indicating device comprising, in combination, a an externally visible transparent reservoir containing a deliquescent compound, said deliquescent compound being opaquely colored below its deliquescent point and being substantially transparent above its deliquescent point, said reservoir overlying and integral with a layer of material having a color which contrasts with the opaque color of the deliquescent compound in said reservoir.

11. A device according to claim 10 wherein said deliquescent compound is an inorganic salt.

12. A device according to claim 11, wherein said salt is solium bromide.

* * * * *

UNITED STATES PATENT AND TRADEMARK OFFICE
CERTIFICATE OF CORRECTION

PATENT NO. : 4,098,120
DATED : July 4, 1978
INVENTOR(S) : Wendell J. Manske

It is certified that error appears in the above-identified patent and that said Letters Patent are hereby corrected as shown below:

Column 10, line 53, per Amendment B dated October 26, 1976, delete "matrix" and insert -- porous pad --;

Signed and Sealed this

Thirteenth Day of February 1979

[SEAL]

Attest:

RUTH C. MASON
Attesting Officer

DONALD W. BANNER
Commissioner of Patents and Trademarks